US009943270B2

(12) United States Patent
Friedman et al.

(10) Patent No.: US 9,943,270 B2
(45) Date of Patent: Apr. 17, 2018

(54) OPTIMIZATION OF PATIENT ALARM SETTINGS FOR MONITORING DEVICES UTILIZING ANALYTICS

(71) Applicant: General Electric Company, Schenectady, NY (US)

(72) Inventors: Bruce Arnold Friedman, Jasper, GA (US); Stephen Thomas Treacy, Milwaukee, WI (US); David Alan Sitzman, Milwaukee, MI (US); Michael John Palmer, Milwaukee, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 164 days.

(21) Appl. No.: 14/755,267

(22) Filed: Jun. 30, 2015

(65) Prior Publication Data

US 2017/0000424 A1    Jan. 5, 2017

(51) Int. Cl.
*A61B 5/00* (2006.01)
*A61B 5/08* (2006.01)
*A61B 5/145* (2006.01)

(52) U.S. Cl.
CPC ............ *A61B 5/746* (2013.01); *A61B 5/0816* (2013.01); *A61B 5/14542* (2013.01)

(58) Field of Classification Search
CPC ... A61B 5/746; A61B 5/0816; A61B 5/14542; A61B 5/0002; A61B 5/14552; A61B 5/7282; A61B 5/745; A61B 5/0205; G08B 21/02; G08B 29/185; G08B 25/016
See application file for complete search history.

(56) References Cited

U.S. PATENT DOCUMENTS

| 7,404,716 B2 | 7/2008 | Gregorio et al. | |
|---|---|---|---|
| 7,963,773 B2 | 6/2011 | Palli et al. | |
| 2003/0028886 A1 | 2/2003 | Wang et al. | |
| 2004/0215069 A1 | 10/2004 | Mannheimer | |
| 2006/0047538 A1* | 3/2006 | Condurso | G06F 19/326 705/3 |
| 2009/0171167 A1* | 7/2009 | Baker, Jr. | A61B 5/0002 600/301 |
| 2009/0234240 A1 | 9/2009 | Kuenzler et al. | |
| 2010/0222653 A1 | 9/2010 | Siejko et al. | |

(Continued)

OTHER PUBLICATIONS

International Search Report and Written Opinion for PCT/US2016/038321, dated Oct. 19, 2016, 15 pages.

*Primary Examiner* — An T Nguyen

(57) ABSTRACT

A monitoring device operable to provide information on data obtained from sensors operably connected between a patient and the device is provided that includes a central processing unit configured to receive incoming data signals from sensors concerning physiological parameters of the patient to compare the incoming data signals to predetermined alarm limits for the physiological parameters to determine an alarm condition and an analytics engine operably connected to the central processing unit and selectively operable to provide predictions of adverse events using the incoming data signals. The central processing unit is configured to alter the alarm limits for at least one of the physiological parameters in response to the activation of the analytics engine to reduce clinically irrelevant alarms.

15 Claims, 5 Drawing Sheets

(56) References Cited

U.S. PATENT DOCUMENTS

| | | | |
|---|---|---|---|
| 2011/0001605 A1* | 1/2011 | Kiani | G06F 19/327 340/5.6 |
| 2011/0105873 A1* | 5/2011 | Feldman | A61B 5/01 600/365 |
| 2011/0118573 A1* | 5/2011 | McKenna | A61B 5/0205 600/323 |
| 2011/0245688 A1* | 10/2011 | Arora | A61B 5/0205 600/483 |
| 2011/0291837 A1* | 12/2011 | Rantala | G06F 19/3431 340/573.1 |
| 2012/0029300 A1* | 2/2012 | Paquet | A61B 5/6833 600/300 |
| 2012/0029301 A1* | 2/2012 | Battista, Jr. | G06F 19/3406 600/300 |
| 2013/0006129 A1* | 1/2013 | Muir | A61B 5/02455 600/500 |
| 2013/0116578 A1* | 5/2013 | An | A61B 5/0205 600/484 |
| 2013/0263855 A1* | 10/2013 | Tivig | A61B 5/4839 128/204.23 |
| 2014/0043164 A1 | 2/2014 | Eschelman et al. | |
| 2014/0142399 A1 | 5/2014 | Al-Ali et al. | |
| 2014/0210631 A1 | 7/2014 | Zavis | |
| 2016/0022140 A1* | 1/2016 | Colman | A61B 5/746 340/539.12 |
| 2016/0051205 A1* | 2/2016 | Al-Ali | A61B 5/7221 600/301 |
| 2016/0093205 A1* | 3/2016 | Boyer | A61B 5/02416 340/506 |
| 2016/0155309 A1* | 6/2016 | Watson | A61B 5/14552 600/324 |
| 2017/0000424 A1* | 1/2017 | Friedman | A61B 5/746 |

\* cited by examiner

OPTIMIZATION OF PATIENT ALARM SETTINGS FOR MONITORING DEVICES UTILIZING ANALYTICS

BACKGROUND OF THE INVENTION

The invention relates generally to monitoring devices and equipment for obtaining and illustrating data about a patient to which the equipment is connected and more particularly to monitoring devices and methods for triggering alarms based on the data from the patient.

In monitoring or diagnostic devices that are currently utilized, the data obtained by the devices is compared to a set limit for the particular physiologic parameter being measured and represented by the incoming data to the device. When the data exceeds the limit, the device is configured to trigger or set off an alarm in order to indicate the current condition of the patient to a treating physician or other medical care professional that is monitoring the patient.

However, in many situations the limits for the triggering of the alarms are set close to the ranges of normal fluctuations of the values for the parameters being monitored, providing a safety net to prevent adverse events from being missed. As such, even when the parameter value only drops below the alarm limit for an instant due to a non-critical event, the device will trigger an alarm based on that sensed value. While setting the alarm limit in this manner is a safeguard against any significant issue or clinically relevant alarm 1002 being missed, the low alarm limit for the monitored parameter also creates a large number of clinically irrelevant alarms 1000, as illustrated in FIG. 3. In FIG. 3, with the alarm limit for a pulse oximetry value detected by a suitable monitoring, device set at 90%, the monitoring device will clearly catch any adverse event that occurs when the event causes the pulse oximetry value for the patient to drop below this threshold.

However, as a result of the closeness of the threshold or alarm limit to the normal or acceptable ranges for this parameter, a large number of clinically irrelevant alarms are generated as well. Further, it is not possible to differentiate the clinically relevant alarms from the clinically irrelevant alarms based on the parameter value alone, such that each alarm event must be acted on in the same manner by the medical personnel monitoring the patient.

One result of the large number of the clinically irrelevant alarm events is the unnecessary expenditure of personnel, time and resources in attending to the clinically irrelevant alarm events. Another result is that certain highly important clinical events could inadvertently be overlooked or missed amidst the normally much larger number of clinically irrelevant alarm events. This is often referred to as alarm fatigue and results from the constant representation of the alarm events in a similar manner that can cause certain events to become "lost" in the flood of alarms and associated information represented on the display screen of the particular device.

As current physiologic limit alarms have a very high false positive rate and setting the limits wider can reduce false positives but at the risk of missing critical events, this risk can be mitigated by the use of analytics in the device to detect patient deterioration (e.g. respiratory depression) which provides more actionable alerts as well as a safety net. In a prior attempt to address this issue, devices have been designed that include analytic engines or analytics that use specific algorithms to correlate multiple sensed parameters from a single patient. This correlation can be utilized to relate the different parameters in a manner that enables the device to predict the adverse event(s) that trigger the alarm based on the trends in the incoming data regarding the sensed parameters.

One particular embodiment of such a system is disclosed in co-pending and co-owned U.S. Non-Provisional patent application Ser. No. 14/101,663, which is expressly incorporated by reference herein in its entirety. As shown in FIG. 2, this analytic uses the respiration rate (RR) and pulse oximetry ($SpO_2$) parameters in a suitable algorithm to predict pending patient respiratory distress in a patient.

However, while this can be a very useful analytic system for predicting respiratory distress events, without changes in the physiological alarm limits for the device the overall alarm burden is not decreased. In particular, looking back at FIG. 3, without any changes to the alarm limits for the parameters used by the analytics, with the $SpO_2$ low default limit 1006 at 90% there still will be a significant number of clinically irrelevant limit alarms 1000 regardless of the determinations/predictions of the adverse events 1004 made by the analytics. Further, in the absence of any additional information, it is difficult to separate clinically relevant alarms 1002 from the irrelevant alarms 1000. This would also be true for other analytics and other parameters used in those analytics, e.g., a hemodynamic analytic based on blood pressure (BP) and pulse rate (PR) or other parameter combinations utilized in or by the algorithms employed in analytics.

Therefore, in order to address alarm fatigue and reduce the number of clinically irrelevant alarms that are generated, it is desirable to develop a monitoring device and associated analytic system that operates or can be configured with variable physiological parameter limits. Such a device and system would allow for the effective determination of an adverse event has occurred with the patient using the analytics, while also allowing for variations in the monitored parameters to limit and/or reduce the number of alarms being triggered for clinically irrelevant events.

BRIEF DESCRIPTION OF THE INVENTION

In various embodiments of the invention, a monitoring device, system and method for monitoring a patient includes a display screen on which data concerning the patient being monitored by the device is illustrated. The incoming data sensed by the device is represented on the display screen to enable an individual viewing the display screen to determine the current physiological parameters of the patient.

The device and display screen can also illustrate various alarm conditions or events, as determined by the device from the incoming data signals received by the device from sensors attached to the item being monitored. The alarm conditions or events are triggered by the comparison of parameter limits stored within the device to the incoming data signals from the sensors. The device also includes an analytics engine or analytics that are operable to enable the device to correlate multiple aspects or attributes of the incoming data signals from the sensors, including but not limited to predetermined maximum and minimum values for the data signals, frequency ranges for the incoming data, as well as correlations between one set of incoming data from one sensor and another set of incoming data from another sensor, such a temporal correspondence, among others. The analytics enable the device to predict the occurrence of an adverse event in the patient based on the predictive algorithm employing the parameters utilized by the analytics. One exemplary embodiment of such an analytics system used in a device of this type is disclosed in co-pending and co-owned U.S. Non-Provisional patent application Ser. No. 14/101,663, which is expressly incorporated by reference herein in its entirety. When an alarm event or condition is determined in this manner by the device, the device modifies the operation of the display concerning the sensed data that created the alarm event or condition to draw the attention of the monitoring individual to those particular data signals.

In one embodiment, the analytics system within the device utilizes the incoming data signals from the patient regarding multiple parameters of the patient that are being monitored by the device in the associated algorithm to predict the onset of an adverse event, such as respiratory distress.

When the analytics system is active, in one exemplary embodiment the device alters the physiological alarm limits for the operation of the device to expand or widen the limits. The limits can be expanded or widened/lowered automatically by the device or in response to input from the operator to the device. Further, the limits for one or more of the parameters utilized by the analytics can be altered individually or together when the analytics are activated on the device.

In another exemplary embodiment, the device can be configured to alter the physiological alarm limits by providing a time delay for the indication of any alarm associated with the parameters utilized by the analytics either in conjunction with or separately from the adjustment of the alarm limits.

In another exemplary embodiment, a method is provided for optimizing the alarm limit settings of a monitoring device operable to provide information on data obtained from sensors operably connected to the device, the method comprising the steps of providing the device including a central processing unit configured to receive incoming data signals from a first sensor concerning a first physiological parameter and from a second sensor concerning a second physiological parameter and to compare the incoming data signals to predetermined alarm limits for the first and second physiological parameters to determine an alarm condition, and an analytics engine operably connected to the central processing unit and selectively operable to provide predictions of adverse events using the incoming data signals; activating the analytics engine; and altering the alarm limits for at least one of the first or second physiological parameters in response to the activation of the analytics engine.

In still another exemplary embodiment, the monitoring device is operable to provide information on data obtained from sensors operably connected between a patient and the device and includes a central processing unit configured to receive incoming data signals from a first sensor concerning a first physiological parameter of the patient and from a second sensor concerning a second physiological parameter of the patient and to compare the incoming data signals to predetermined alarm limits for the first and second physiological parameters to determine an alarm condition and an analytics engine operably connected to the central processing unit and selectively operable to provide predictions of adverse events using the incoming data signals, wherein the central processing unit is configured to alter the alarm limits for at least one of the first or second physiological parameters in response to the activation of the analytics engine.

In still a further exemplary embodiment, the medical monitoring device for providing information about patient operably connected to the device includes an electronic storage medium in which values for alarm limits for a number of physiological parameters to be monitored are stored, a central processing unit operably connected to the electronic storage medium and configured to receive incoming data signals concerning the parameters of the patient and to compare the incoming data signals to the alarm limits for the parameters to determine an alarm condition, one or more sensors operably connected to the central processing unit and adapted to be connected to the patient to obtain and transmit the incoming data signals on the parameters to be monitored from the patient to the central processing unit, an analytics engine operably connected to the central processing unit and selectively operable to provide predictions of adverse events using the incoming data signals and a display operably connected to the central processing unit, the display including a display screen and a user interface configured to enable the selective activation of the analytics engine, wherein the central processing unit is configured to alter the alarm limit for at least one physiological parameter in response to the activation of the analytics engine.

It is to be understood that both the foregoing general description and the following detailed description are exemplary and explanatory and are intended to provide further explanation of the invention as claimed.

DETAILED DESCRIPTION OF THE INVENTION

Figure 1:
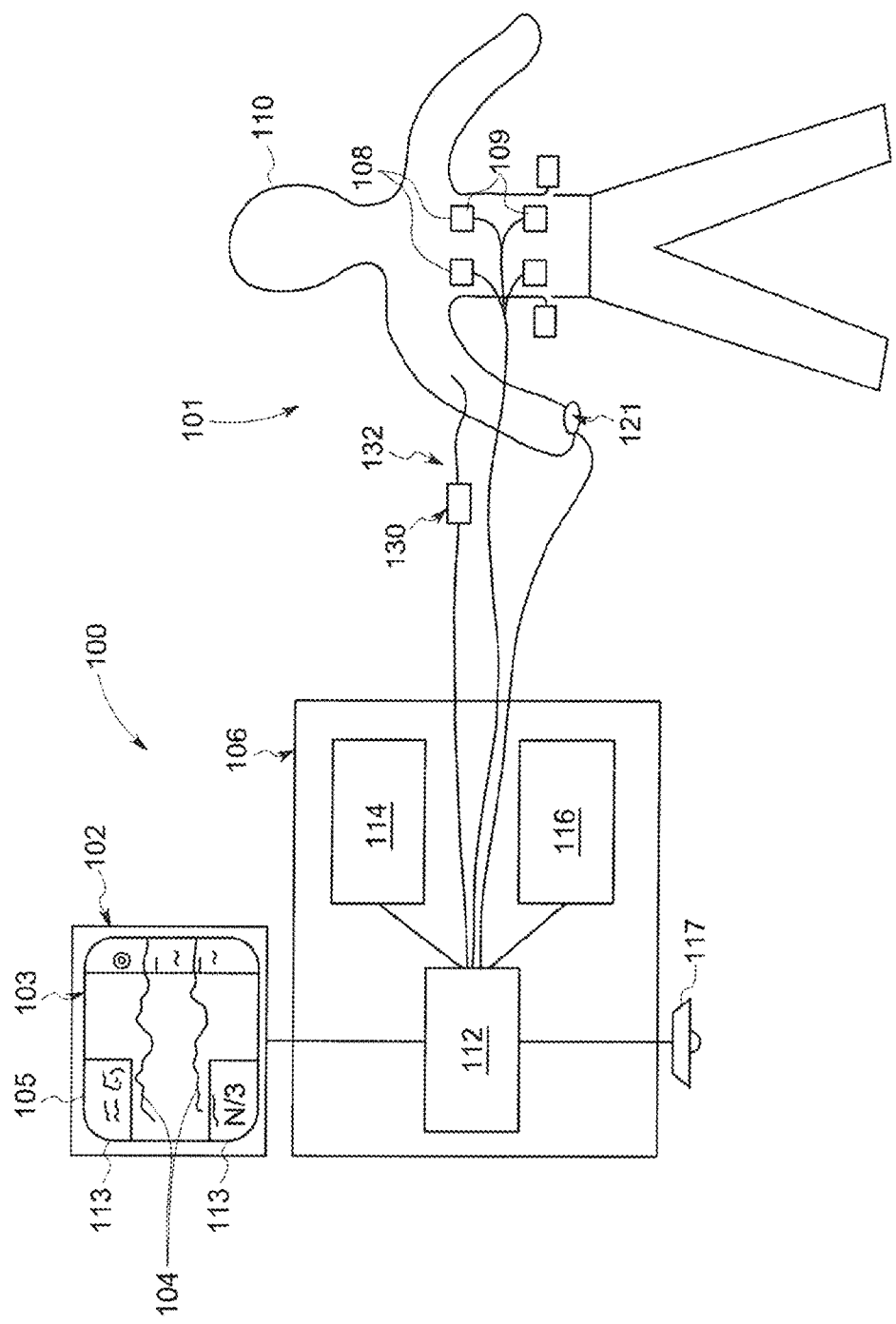
FIG. 1 is a schematic view of a monitoring device in accordance with an exemplary embodiment of the invention.
Figure 2:
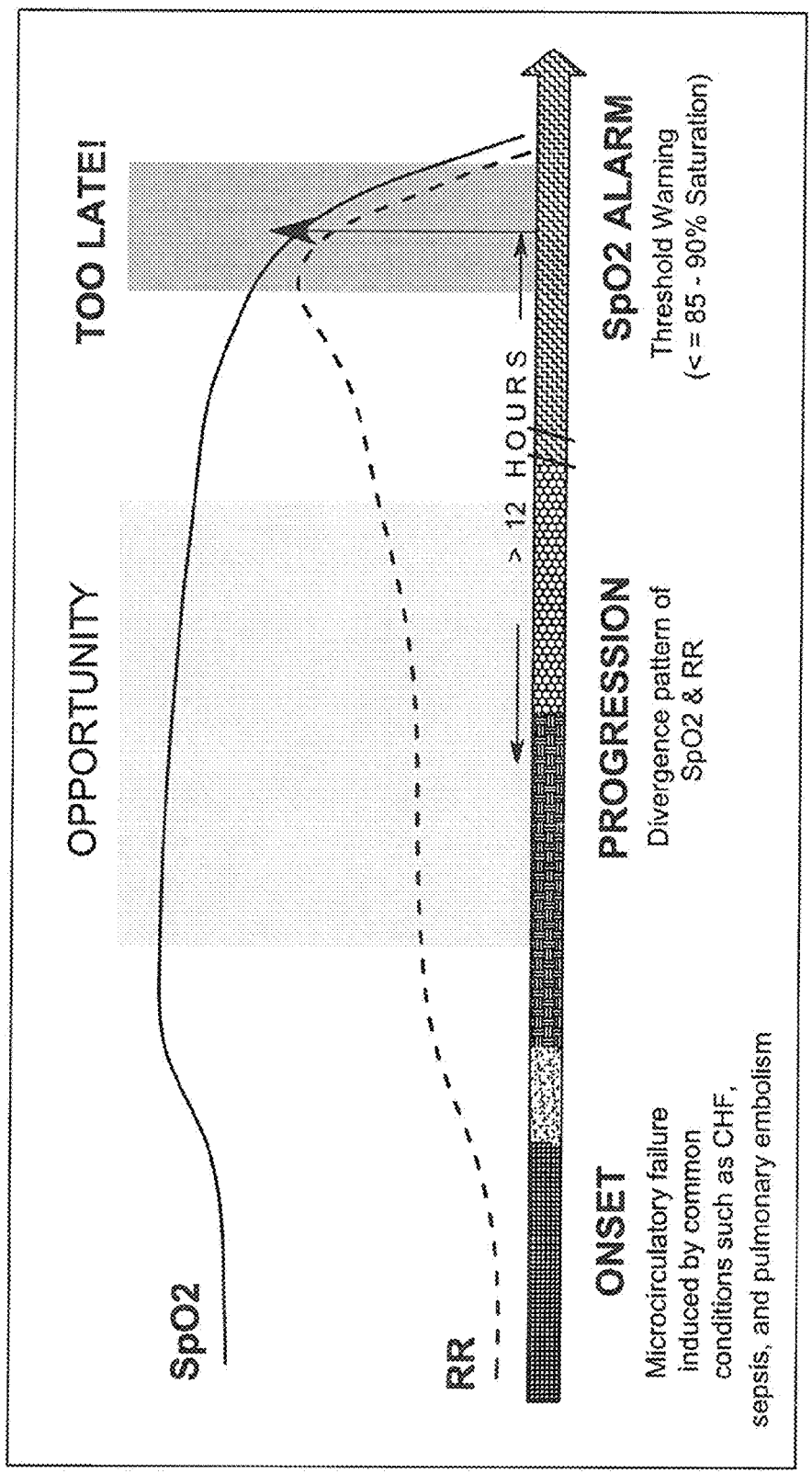
FIG. 2 graphically illustrates the operation of an exemplary analytics engine utilized with the monitoring device of FIG. 1.

FIG. 1 illustrates an exemplary embodiment of the invention which includes a monitoring or diagnostic device and system 100, which can be any suitable type of monitoring device for monitoring various operating parameters of an object, machine, individual or other item 101 operably connected to the device 100. The device 100 includes a display 102 of any suitable type, such as a touch screen display, having a screen 103 thereon on which the monitoring data signals 104 regarding the object 101 connected to the device 100 can be displayed. When formed as a touch screen, the display 102 can additionally function as a user interface 105 for use in controlling the operation of the device 100, though the interface 105 can be formed as a separate component connected to the device 100, if desired.

In the exemplary embodiment of FIG. 1, the device 100 takes the form of a medical monitoring device 106 that has one or more leads or sensors 108, such as impedance respiration/respiratory sensors 109, operably connected in any suitable manner between the medical monitoring device 106 and a patient 110 in order to monitor various vital statistics of the patient 110. In addition to the sensors 109, the device 100 can employ additional sensors 108 used to monitor other parameters or statistics of the patient 110, such as a pulse oximeter sensor 121 and/or an invasive pressure catheter 130 and invasive pressure transducer 132 to measure the blood flow and pressure of the patient 110 for comparison with the data obtained from the sensors 109.

The medical monitoring device 106 includes a central processing unit (CPU) 112 operably connected to the sensors 108 in order to receive and process data from, the sensors 108 on the various vital statistics or parameters of specified bodily functions of the patient 110, which in the exemplary embodiment of FIG. 1 relates to respiratory functions, though other bodily functions or systems are also contemplated as being within the scope of the present invention. These parameters can then be transmitted from the CPU 112 to the display 102 for presentation in a specified manner on the screen 103 of the display 102 for review by an individual monitoring the patient 110 via the display 102. Alternatively, the CPU 112 can be operably connected, such as by wired or wireless connections, to a network (not shown) that permits the use of multiple visual interfaces (not shown) including those such as a television, health monitor, iPhone or similar device, laptop, portable electronics, among others. This integration of the monitoring device 100 into a system with personal computing devices and portable electronics expands the communication capabilities between clinicians, as well as to facilitate patient observation from remote locations, e.g., central staff stations.

The device 100 also includes memory module 114, which can take the form of any suitable computer-readable storage media, for example a RAM module, and an analytics engine 116, each of which are operably connected to the CPU 112 in order to assist in the monitoring function of the device 100 using the data signals 104 supplied to the CPU 112 via the sensors 108. The device 100 also includes an audio speaker 117 for enabling the device 100 to provide audible indications of various operating characteristics of the device 100.

The storage media 114 can include certain information regarding the predetermined normal or acceptable ranges for the operating parameters, vital statistics or physiological parameters for the patient 110 to which the device 100 is connected. These stored ranges can be utilized by the CPU 112 in conjunction with the incoming data signals 104 from the sensors 108 and the personal statistics of the patient 110 to determine the current vital statistics or physiological parameters of the patient 110 and whether those vital statistics or physiological parameters are outside of the predetermined ranges for those particular vital statistics or physiological parameters. The stored ranges for the incoming data signals 104 on the different physiological parameters and vital statistics received by the CPU 112 from the various sensors 108 can include ranges for minimum and maximum absolute values of the sensed parameters, minimum and maximum frequency ranges for the sensed physiological parameters, or any other suitable aspect of the incoming data signals 104 to be used in the determination of an alarm event or condition.

The analytics engine 116 is operable within the device 100 to utilize one or a combination of the incoming data signals 104 from the CPU 112 in a suitable manner to provide a prediction of any adverse event, such as respiratory distress, for the patient. While the particular functioning of or algorithm utilized in the engine 116 can be varied as desired to utilize any number of different combinations of incoming data signals 104, one exemplary embodiment of a suitable analytics engine 116 is disclosed in co-pending and co-owned U.S. Non-Provisional patent application Ser. No. 14/101,663, which is expressly incorporated by reference herein in its entirety. In this exemplary embodiment of the engine 116, the incoming data signals 104 relating to the $SpO_2$ and RR of the patient are combined in order to provide the operator with a predictive indicator of the occurrence of respiratory distress in the patient 110.

The operation of the analytics engine 116 using the incoming data signals 104 occurs in conjunction with the operation of the CPU 112 in comparing the incoming data signals 104 with the alarm limits stored in the media 114. Thus, separate from the determination made by the analytics engine 116 with regard to the prediction of any respiratory distress, the CPU 112 is actively comparing the individual incoming data signals 104 to the alarm limits stored in media 114.

Figure 3:
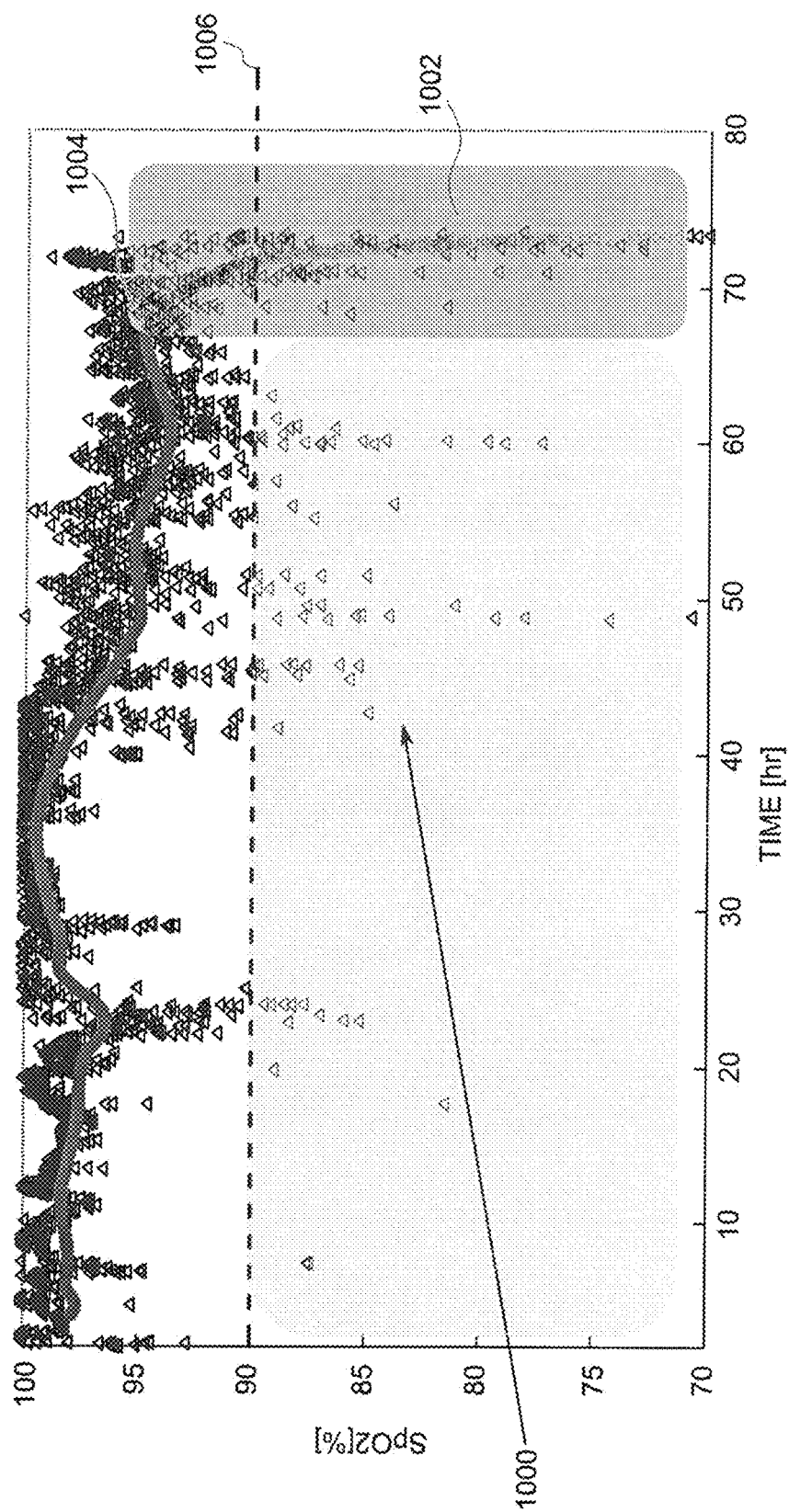
FIG. 3 graphically illustrates exemplary $SpO_2$ parameter values over time for a patient as measured by the monitoring device using default $SpO_2$ alarm limits.
Figure 4:
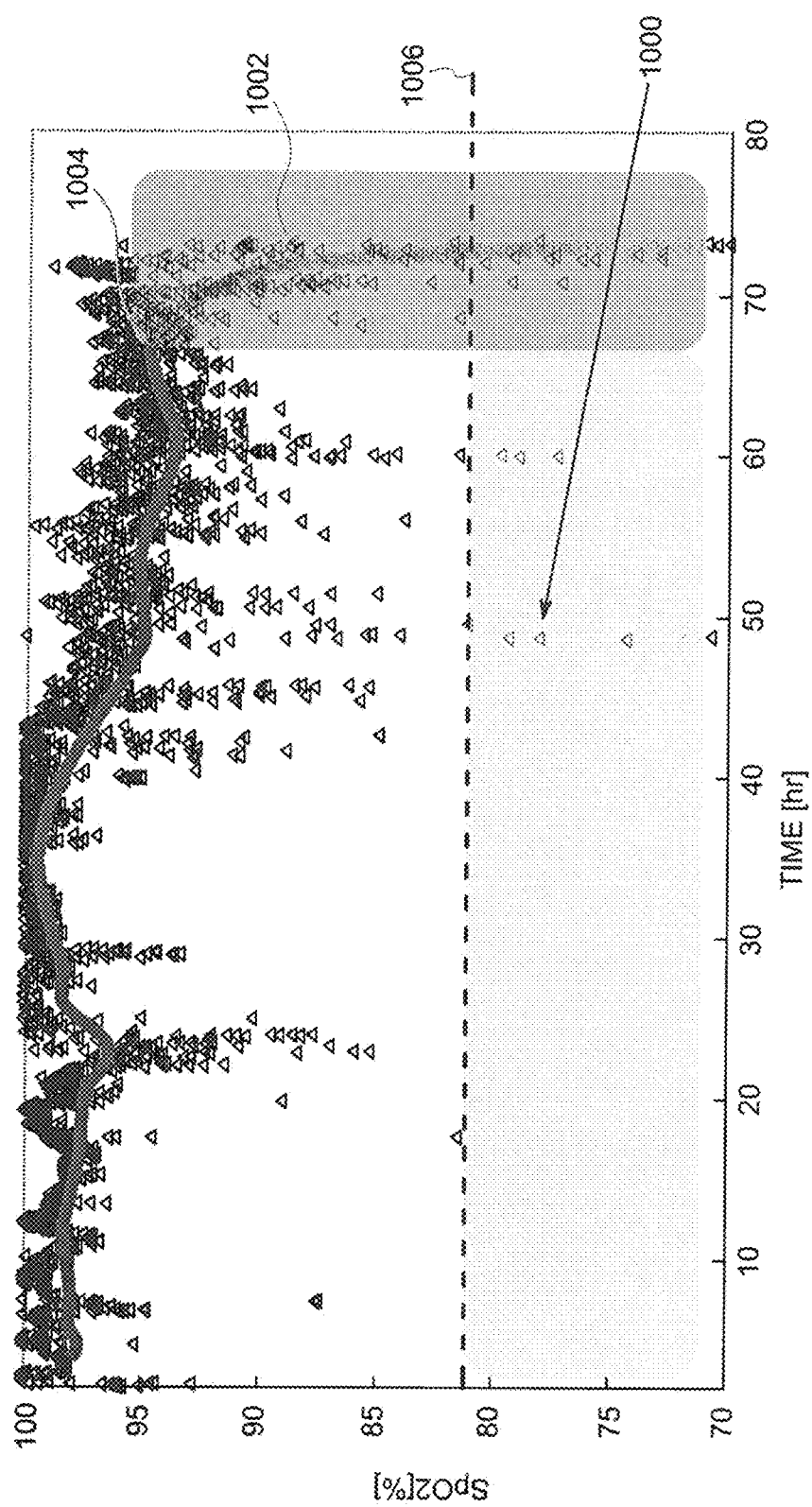
FIG. 4 graphically illustrates exemplary $SpO_2$ parameter values over time for a patient as measured by the monitoring device using modified $SpO_2$ alarm limits in accordance with an exemplary embodiment of the invention.

However, in order to reduce the number of clinically irrelevant alarms generated by the device 100, when the analytics engine 116 is activated, e.g., through the user interface 105, the CPU 112 of the device 100 is configured to alter the alarm limits of one or more of the parameters being utilized by the analytics engine 116. In one embodiment, when the analytics engine 116 is activated by an operator, the CPU 112 automatically alters the alarm limits for at least one of the parameters sensed by the device 110 and utilized by the analytics engine 116. Referring to FIGS. 3 and 4, FIG. 3 represents the operation of the device 100 without use of the analytics engine 116 and an alarm limit for $SpO_2$ of 90%, resulting in a very significant number of clinically irrelevant alarms 1000. However, when the analytics engine 116 is activated, the CPU 112 can alter the lower limit of the parameter to 81%, as shown in FIG. 4, which is the $SpO_2$ parameter in the illustrated example, thereby significantly reducing the number of clinically irrelevant alarms 1000 that are generated by the device 100.

While the above example shows the device 100 as automatically adjusting or optimizing the alarm limit settings when the analytic engine 116 is activated, the device 100 can alternatively actively prompt the operator when the analytics 116 are activated for adjustment or optimization of the alarm limit(s) as desired by the operator. In this embodiment, the device 100 can prompt the operator to accept or approve of the alarm limit alteration programmed into the device 100, or the user can alternatively be prompted to enter a desired or modified alarm limit to optimize the alarm limit settings for the device 100, optionally within a range of acceptable alterations stored in media 114, for use with the selected parameter(s) while the analytics engine 116 is active.

In another exemplary embodiment, either separate from or in conjunction with the alteration of the alarm limits, the CPU 112 can be configured to activate a pre-determined delay for the alarm to be indicated or sounded by the device 100 via the display 102 and/or speaker 117. The time delay in this embodiment can be pre-determined, e.g., thirty (30) seconds, or can alternatively be selected by the operator to optimize the operation alarm limits for the device 100, optionally within specified ranges of time for the delay stored in media 114.

Additionally, in any of the above described exemplary embodiments, once the analytics engine 116 is switched off or disabled by the operator, the device 100 automatically resets the alarm limits to the default levels, i.e., as illustrated in FIG. 3 concerning the illustrated exemplary embodiment of the device 100 represented in FIGS. 3 and 4.

Figure 5:
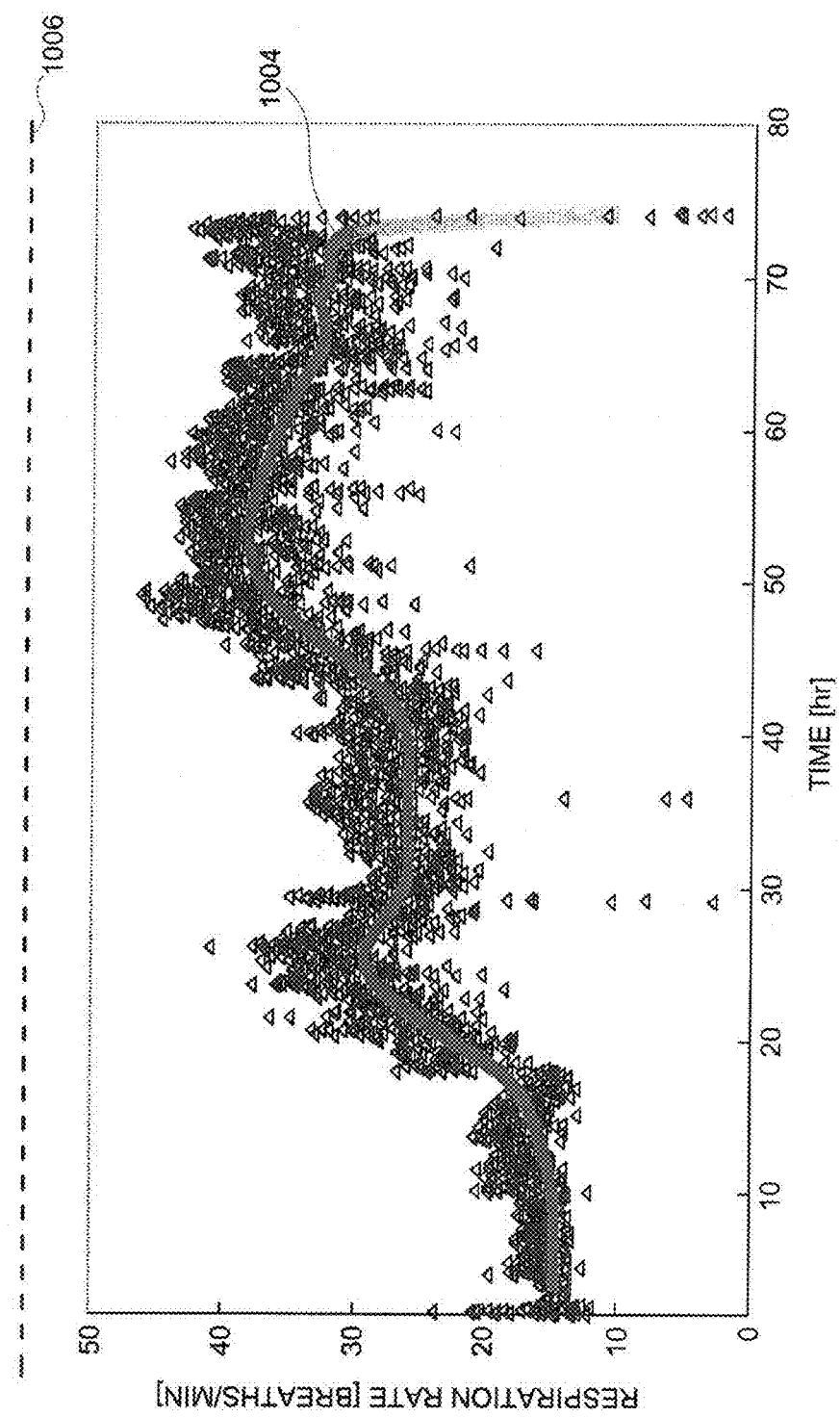
FIG. 5 graphically illustrates exemplary RR parameter values over time for a patient as measured by the monitoring device using default RR alarm limits.

While the above described examples illustrate the changes in the alarm limits used by the device 100 when a single parameter is altered, in other situations the limits for one of the parameters being utilized by the analytics 116 may not be readily alterable in the manners illustrated above. For example, as shown in FIG. 5, the RR default high limit 1006 is set to 60 bpm, which effectively makes it useless in the determination of any adverse events due to the high level of noise in that parameter. In addition, significant changes normally occur in the RR value over the hour of monitoring prior to the occurrence of the adverse event 1004. As such, selecting an alarm limit that would be clinically useful for the RR parameter can be difficult.

To accommodate for these situations, in one exemplary embodiment, when the analytics engine 116 is activated, the CPU 112 can disable all single parameter limit alarms for those parameters being used by the analytic engine 116. Instead, the CPU 112 will only trigger a limit alarm if the alarm limits are violated in each of the multiple parameters used in the algorithm employed in the analytic engine 116, such as the RR and SpO2 for the illustrated example in FIGS. 3 and 4. In other words, the device 100 alters the alarm limits by associating the alarm limits for both of the first (RR) and second (SpO2) physiological parameters with one another to form a combined alarm limit that is triggered when the alarm limits for both of the first and second physiological parameters are exceeded. An alternative exemplary embodiment of this device 100 employs a time delay either separately from or in conjunction with the requirement that each or the combined parameter alarm limits be violated.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for optimizing alarm settings, the method comprising:
   receiving incoming data signals from a first sensor concerning a first physiological parameter and from a second sensor concerning a second physiological parameter of a patient;
   determining whether an analytics engine is activated, wherein the analytics engine, when activated, predicts adverse events for the patient using the incoming data signals concerning the first physiological parameter and the second physiological parameter;
   in response to determining that the analytics engine is not activated, applying a first alarm setting to the incoming data signals for triggering alarms;
   in response to determining that the analytics engine is activated, applying a second alarm setting to the incoming data signals for triggering alarms, wherein the second alarm setting is different from the first alarm setting; and
   wherein applying the first alarm setting comprises: comparing the incoming data signals concerning the first physiological parameter to an alarm limit for the first physiological parameter;
   comparing the incoming data signals concerning the second physiological parameter to an alarm limit for the second physiological parameter; and
   triggering an alarm if either the alarm limit for the first physiological parameter or the alarm limit for the second physiological parameter is exceeded; applying the second alarm setting comprises:
   comparing the incoming data signals concerning the first physiological parameter to an alarm limit for the first physiological parameter;
   comparing the incoming data signals concerning the second physiological parameter to an alarm limit for the second physiological parameter; and
   triggering an alarm if both the alarm limit for the first physiological parameter and the alarm limit for the second physiological parameter are exceeded.

2. The method of claim 1, wherein the first physiological parameter is peripheral oxygen saturation, the second physiological parameter is respiration rate, and the adverse events include respiratory distress.

3. The method of claim 1, wherein applying the first alarm setting comprises comparing the incoming data signals concerning the first physiological parameter to a first alarm limit, applying the second alarm setting comprises comparing the incoming data signals concerning the first physiological parameter to a second alarm limit, the second alarm limit triggers fewer alarms than the first alarm limit.

4. The method of claim 3, further comprising:
   in response to determining that the analytics engine is activated, prompting for an input for the second alarm limit.

5. The method of claim 3, further comprising:
   in response to determining that the analytics engine is activated, adding a time delay to triggering an alarm.

6. A monitoring device comprising:
   a central processing unit configured to receive incoming data signals from a first sensor concerning a first physiological parameter and from a second sensor concerning a second physiological parameter of a patient; and
   an analytics engine operably connected to the central processing unit and configured to predicts adverse events for the patient using the incoming data signals concerning the first physiological parameter and the second physiological parameter when being activated;
   wherein the central processing unit is further configured to: determine whether the analytics engine is activated;
   in response to determining that the analytics engine is not activated, apply a first alarm setting to the incoming data signals for triggering alarms;
   in response to determining that the analytics engine is activated, apply a second alarm setting to the incoming data signals for triggering alarms, wherein the second alarm setting is different from the first alarm setting; and
   wherein applying the first alarm setting comprises:
   comparing the incoming data signals concerning the first physiological parameter to an alarm limit for the first physiological parameter;
   comparing the incoming data signals concerning the second physiological parameter to an alarm limit for the second physiological parameter; and
   triggering an alarm if either the alarm limit for the first physiological parameter or the alarm limit for the second physiological parameter is exceeded; applying the second alarm setting comprises:
   comparing the incoming data signals concerning the first physiological parameter to an alarm limit for the first physiological parameter;
   comparing the incoming data signals concerning the second physiological parameter to an alarm limit for the second physiological parameter; and triggering an alarm if both the alarm limit for the first physiological parameter and the alarm limit for the second physiological parameter are exceeded.

7. The monitoring device of claim 6, wherein the first physiological parameter is peripheral oxygen saturation, the second physiological parameter is respiration rate, and the adverse events include respiratory distress.

8. The monitoring device of claim 6, wherein applying the first alarm setting comprises comparing the incoming data signals concerning the first physiological parameter to a first alarm limit, applying the second alarm setting comprises comparing the incoming data signals concerning the first physiological parameter to a second alarm limit, the second alarm limit triggers fewer alarms than the first alarm limit.

9. The monitoring device of claim 8, wherein the central processing unit is further configured to:
   in response to determining that the analytics engine is activated, prompt for an input for the second alarm limit.

10. The monitoring device of claim 8, wherein the central processing unit is further configured to:
    in response to determining that the analytics engine is activated, add a time delay to triggering an alarm.

11. A non-transitory computer readable medium comprising instructions which, when executed by a central processing unit, cause the central processing unit to perform operations comprising:
    receiving incoming data signals from a first sensor concerning a first physiological parameter and from a second sensor concerning a second physiological parameter of a patient;
    determining whether an analytics engine is activated, wherein the analytics engine, when activated, predicts adverse events for the patient using the incoming data signals concerning the first physiological parameter and the second physiological parameter;
    in response to determining that the analytics engine is not activated, applying a first alarm setting to the incoming data signals for triggering alarms;
    in response to determining that the analytics engine is activated, applying a second alarm setting to the incoming data signals for triggering alarms, wherein the second alarm setting is different from the first alarm setting; and
    wherein applying the first alarm setting comprises:
    comparing the incoming data signals concerning the first physiological parameter to an alarm limit for the first physiological parameter;
    comparing the incoming data signals concerning the second physiological parameter to an alarm limit for the second physiological parameter; and
    triggering an alarm if either the alarm limit for the first physiological parameter or the alarm limit for the second physiological parameter is exceeded;
    applying the second alarm setting comprises:
    comparing the incoming data signals concerning the first physiological parameter to an alarm limit for the first physiological parameter;
    comparing the incoming data signals concerning the second physiological parameter to an alarm limit for the second physiological parameter; and
    triggering an alarm if both the alarm limit for the first physiological parameter and the alarm limit for the second physiological parameter are exceeded.

12. The medium of claim 11, wherein the first physiological parameter is peripheral oxygen saturation, the second physiological parameter is respiration rate, and the adverse events include respiratory distress.

13. The medium of claim 11, wherein applying the first alarm setting comprises comparing the incoming data signals concerning the first physiological parameter to a first alarm limit, applying the second alarm setting comprises comparing the incoming data signals concerning the first physiological parameter to a second alarm limit, the second alarm limit triggers fewer alarms than the first alarm limit.

14. The medium of claim 13, wherein the operations further comprise:
    in response to determining that the analytics engine is activated, prompting for an input for the second alarm limit.

15. The medium of claim 13, wherein the operations further comprise:
    in response to determining that the analytics engine is activated, adding a time delay to triggering an alarm.

* * * * *